US011448642B2

(12) United States Patent
Warr et al.

(10) Patent No.: US 11,448,642 B2
(45) Date of Patent: Sep. 20, 2022

(54) METHOD FOR IDENTIFYING MALODOUR COUNTERACTANTS

(71) Applicant: TAKASAGO INTERNATIONAL CORPORATION, Tokyo (JP)

(72) Inventors: Jonathan Warr, Paris (FR); Marcel Winnig, Milan (IT)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 432 days.

(21) Appl. No.: 16/468,522

(22) PCT Filed: Dec. 14, 2017

(86) PCT No.: PCT/JP2017/044979
§ 371 (c)(1),
(2) Date: Jun. 11, 2019

(87) PCT Pub. No.: WO2018/110672
PCT Pub. Date: Jun. 21, 2018

(65) Prior Publication Data
US 2021/0181180 A1 Jun. 17, 2021

(30) Foreign Application Priority Data
Dec. 14, 2016 (EP) .................... 16306680

(51) Int. Cl.
*G01N 33/50* (2006.01)
*G01N 33/566* (2006.01)
(52) U.S. Cl.
CPC ....... *G01N 33/5008* (2013.01); *G01N 33/566* (2013.01); *G01N 2333/726* (2013.01)
(58) Field of Classification Search
CPC ............. G01N 33/566; G01N 33/5008; G01N 2333/726
See application file for complete search history.

(56) References Cited

U.S. PATENT DOCUMENTS

| | | | |
|---|---|---|---|
| 2003/0207337 A1 | 11/2003 | Han et al. | |
| 2013/0216492 A1 | 8/2013 | Kato et al. | |
| 2014/0186864 A1 | 7/2014 | Kato et al. | |
| 2015/0005177 A1 | 1/2015 | Pfister et al. | |
| 2015/0260707 A1 | 9/2015 | Ashtibaghaei et al. | |
| 2017/0285009 A1 | 10/2017 | Rodriguez et al. | |
| 2018/0208637 A1 | 7/2018 | Pfister et al. | |

FOREIGN PATENT DOCUMENTS

| | | | |
|---|---|---|---|
| EP | 2 832 347 A1 | 2/2015 | |
| JP | 2012-249614 A | 12/2012 | |
| JP | 2016-523546 A | 8/2016 | |
| JP | 2017-528120 A | 9/2017 | |
| WO | 2014/191047 A1 | 12/2014 | |
| WO | 2016/030378 A1 | 3/2016 | |

OTHER PUBLICATIONS

March et al. Structure-odour relationships reviewed in the postgenomic era: olfactory receptors and odourants. Flavour and Fragnance Journal, 2015, vol. 30, No. 5., pp. 1-35. (Year: 2015).*
Office Action dated Sep. 14, 2021 by the Japan Patent Office in counterpart Japanese Patent Machine Application No. 2019-531492.
Office Action dated Feb. 15, 2022, issued by the Japan Patent Office in Japanese Patent Application Machine No. 2019-531492.
Malnic, B., et al., "Combinatorial Receptor Codes for Odors", Mar. 5, 1999, Cell, vol. 96, p. 713-723, 11 pages total.
Glusman, G., et al., "The olfactory receptor gene superfamily: Data mining, classification, and nomenclature", Dec. 2000, Mammalian Genome 11, p. 1016-1023, 9 pages total.
Duan, X., et al., "Crucial role of copper in detection of metal-coordinating odorants", Feb. 28, 2012, PNAS. vol. 109, No. 9, p. 3492-3497, 6 pages total.
Troccaz, Myriam, "The biosynthetic pathway of sulfur-containing molecules in Human Axillary Malodor from precursors to odorous volatiles", Jun. 18, 2009, These de doctorat: Univ. Geneve, No. Sc. 4102 https://archive-ouverte.unige.ch/unige:4563, 195 pages total.
Natsch, A., et al., "Identification of Odoriferous Sulfanylalkanols in Human Axilla Secretions and Their Formation through Cleavage of Cysteine Precursors by a C—S Lyase Isolated from Axilla bacteria", 2004, Chemistry & Biodiversity, vol. 1, p. 1058-1072, 15 pages total.
Denawaka, C., et al., "Source, impact and removal of malodour from soiled clothing", Feb. 15, 2016, Journal of Chromatography A, 1438, p. 216-225, 10 pages total.
Troccaz, M., et al., "The influence of thermal reaction and microbial transformation on the odour of human urine", Jan. 25, 2013, Flavour and Fragrance Journal, 28, p. 200-211, 12 pages total.
Li, S., et al., "Smelling Sulfur: Copper and Silver Regulate the Response of Human Odorant Receptor OR2T11 to Low-Molecular-Weight Thiols", Sep. 23, 2016, Journal of the American Chemical Society, 138, p. 13281-13288, 8 pages total.
Noe, F., et al., "OR2M3: A Highly Specific and Narrowly Tuned Human Odorant Receptor for the Sensitive Detection of Onion Key Food Odorant 3-Mercapto-2-methylpentan-1-ol", 2017, Chemical Senses, vol. 42. No. 3, p. 195-210, 16 pages total.
Saito, H., et al., "RTP Family Members Induce Functional Expression of Mammalian Odorant Receptors", Nov. 24, 2004, Cell, vol. 119, p. 679-691, 13 pages total.
Von Dannecker, L., et al., "Ric-8B, an Olfactory Putative GTP Exchange Factor, Amplifies Signal Transduction through the Olfactory-Specific G-Protein Gaolf", Apr. 13, 2005, The Journal of Neuroscience, vol. 25, No. 15, p. 3793-3800, 8 pages total.
Von Dannecker, L., et al., "Ric-8B promotes functional expression of odorant receptors", Jun. 13, 2006, PNAS, vol. 103, No. 24, p. 9310-9314, 5 pages total.

(Continued)

*Primary Examiner* — Shafiqul Haq
(74) *Attorney, Agent, or Firm* — Sughrue Mion, PLLC

(57) ABSTRACT

The invention relates to a method for determining whether a test compound can counteract malodour from a sulphur odorant. The method includes contacting the test compound and the sulphur odorant with an olfactory receptor OR4E2, and comparing the binding of the OR4E2 to the sulphur odorant, or the activity of the OR4E2, in the presence and in the absence of the test compound.

9 Claims, 7 Drawing Sheets

Specification includes a Sequence Listing.

(56) References Cited

OTHER PUBLICATIONS

Bufe, B., et al., "The human TAS2R16 receptor mediates bitter taste in response to β-glucopyranosides", Nov. 2002, Nature Genetics, vol. 32, p. 397-401, 5 pages total.
Search Report dated Feb. 8, 2018, issued by the International Searching Authority in International Application No. PCT/JP2017/044979 (PCT/ISA/210).
Written Opinion dated Feb. 8, 2018, issued by the International Searching Authority in International Application No. PCT/JP2017/044979 (PCT/ISA/237).
Communication dated Mar. 17, 2017, issued by the European Patent Office in counterpart European Application No. 16 30 6680.
Office Action dated May 10, 2022 by the Japanese Patent Office in counterpart Japanese Patent Application No. 2019-531492.

* cited by examiner

[Fig. 1A]
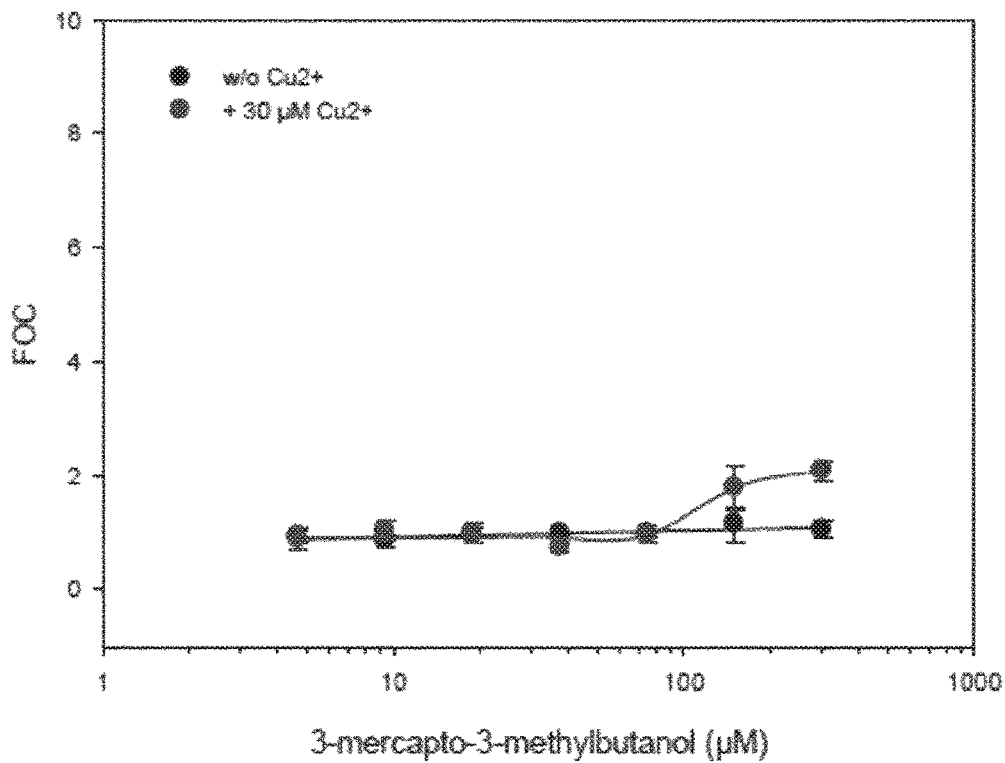
[Fig. 1B]
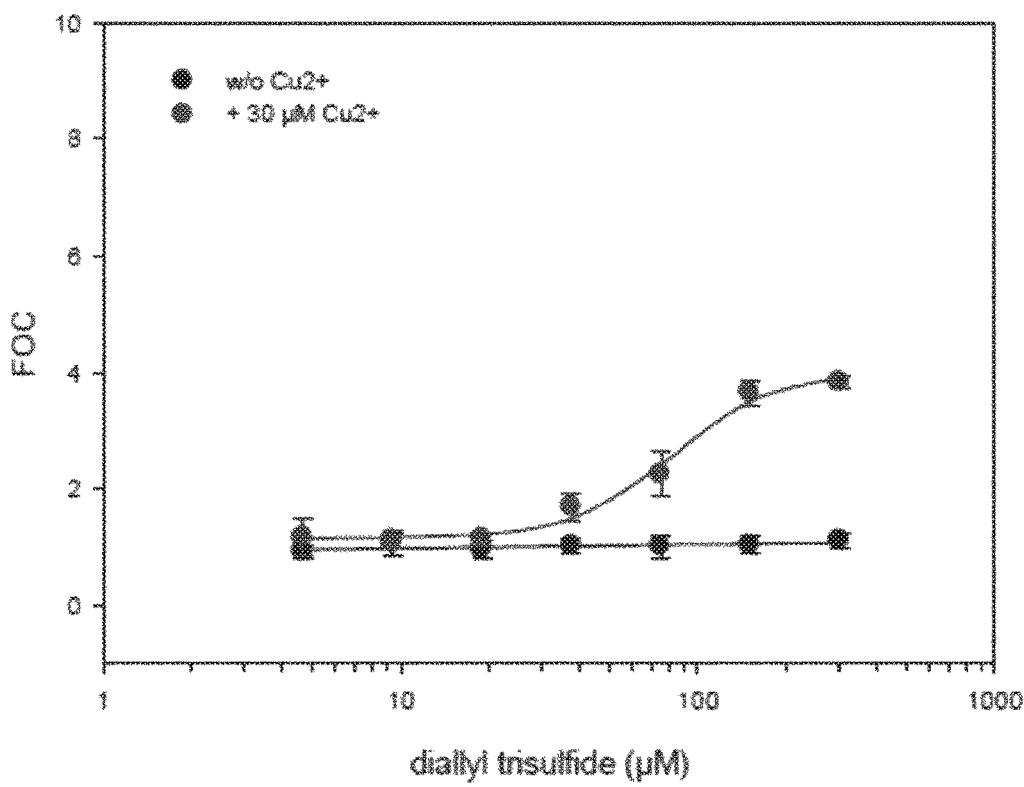

[Fig. 2A]
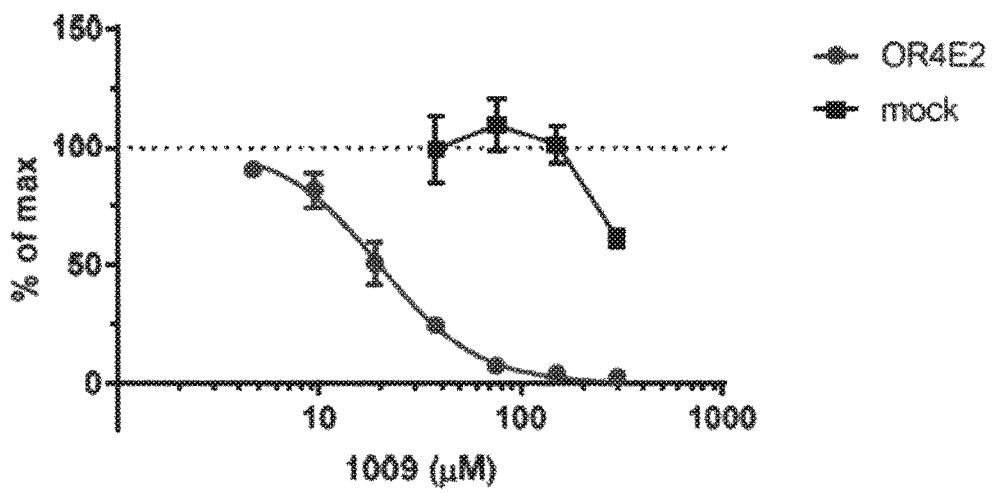
[Fig. 2B]
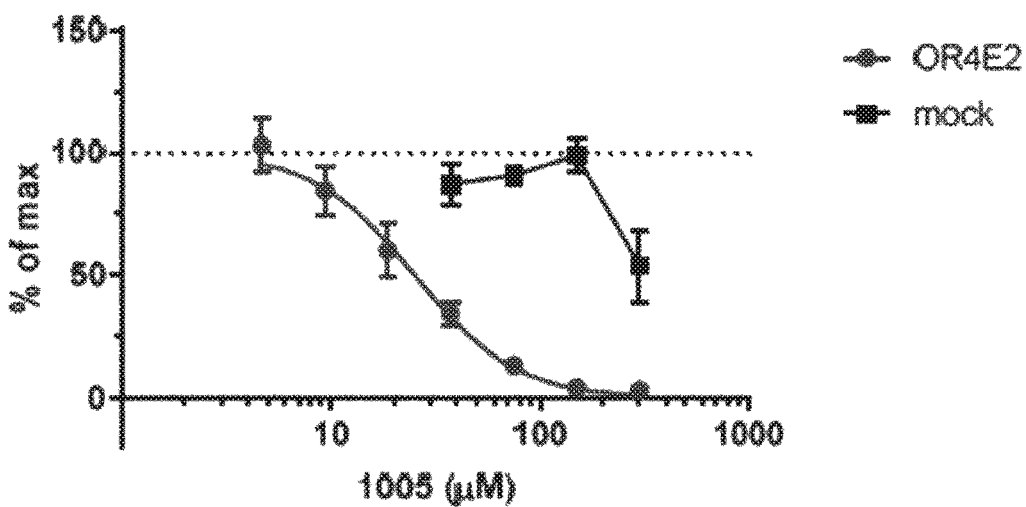

[Fig. 3A]
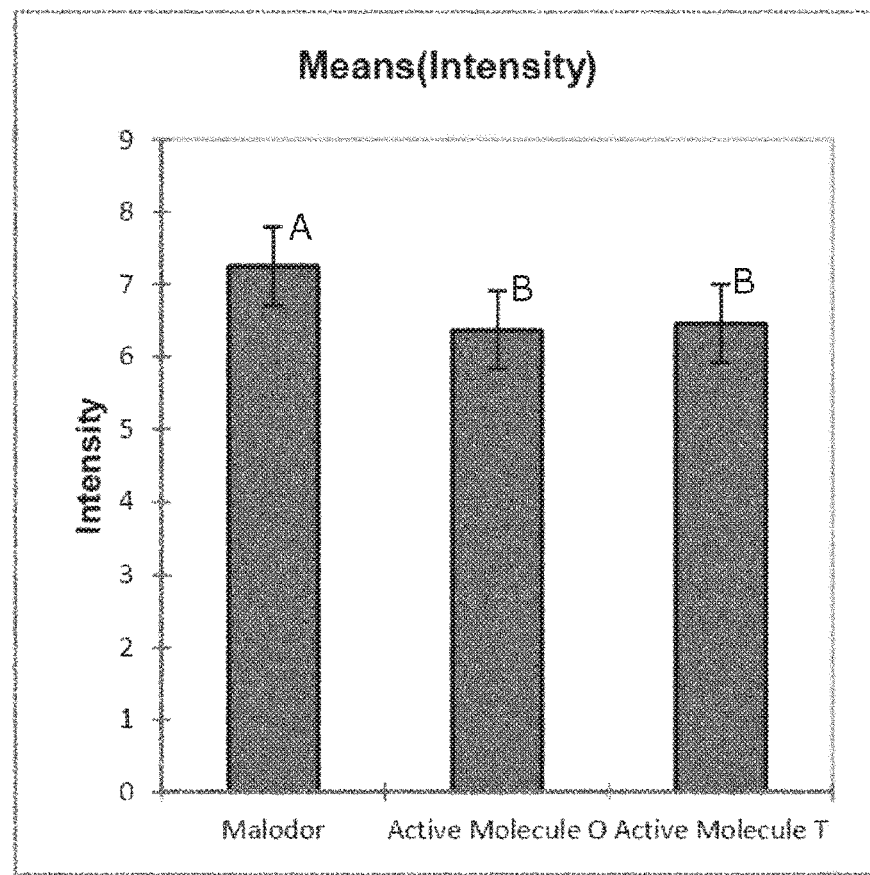

[Fig. 3B]
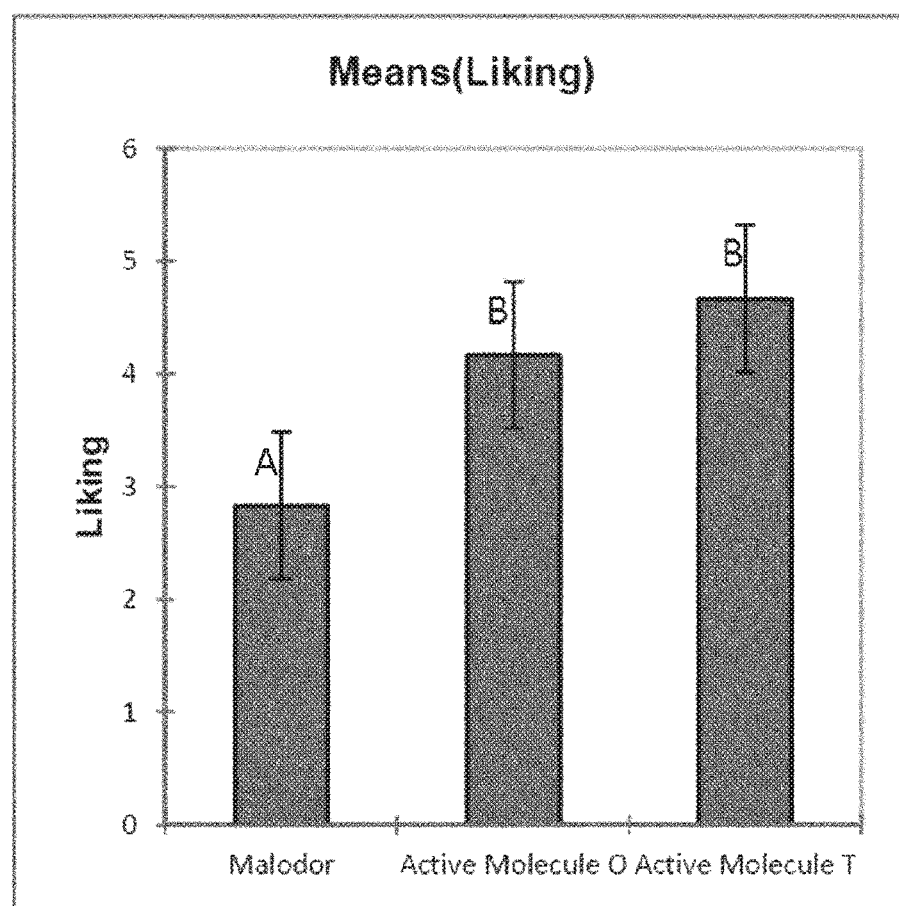

[Fig. 4A]
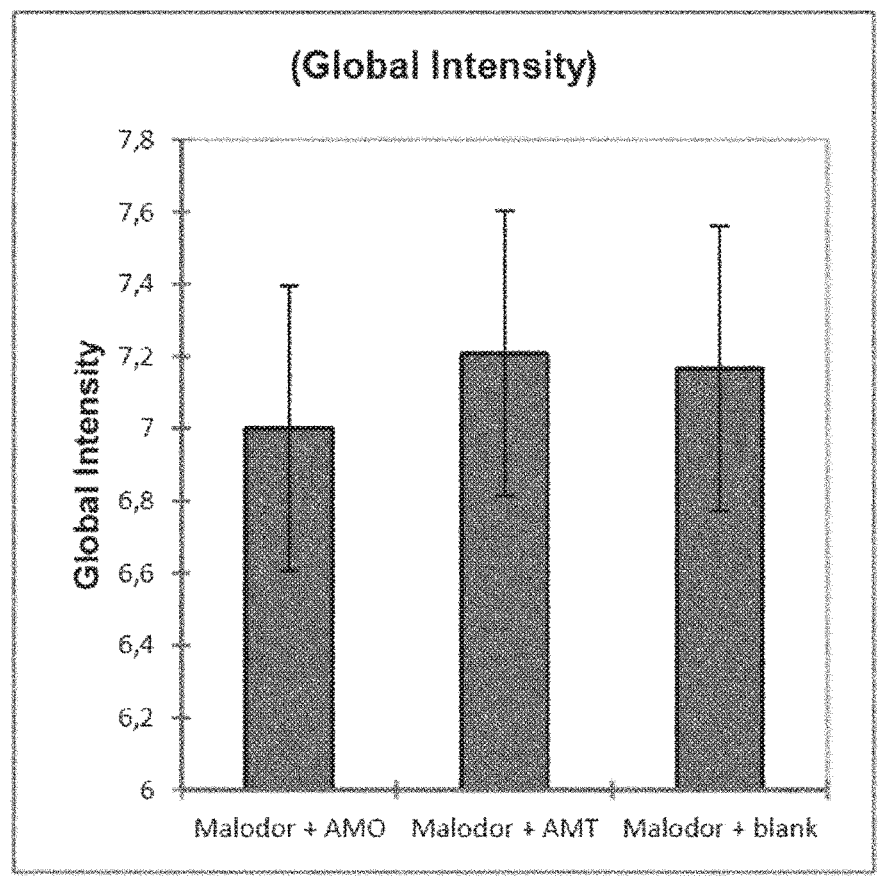

[Fig. 4B]
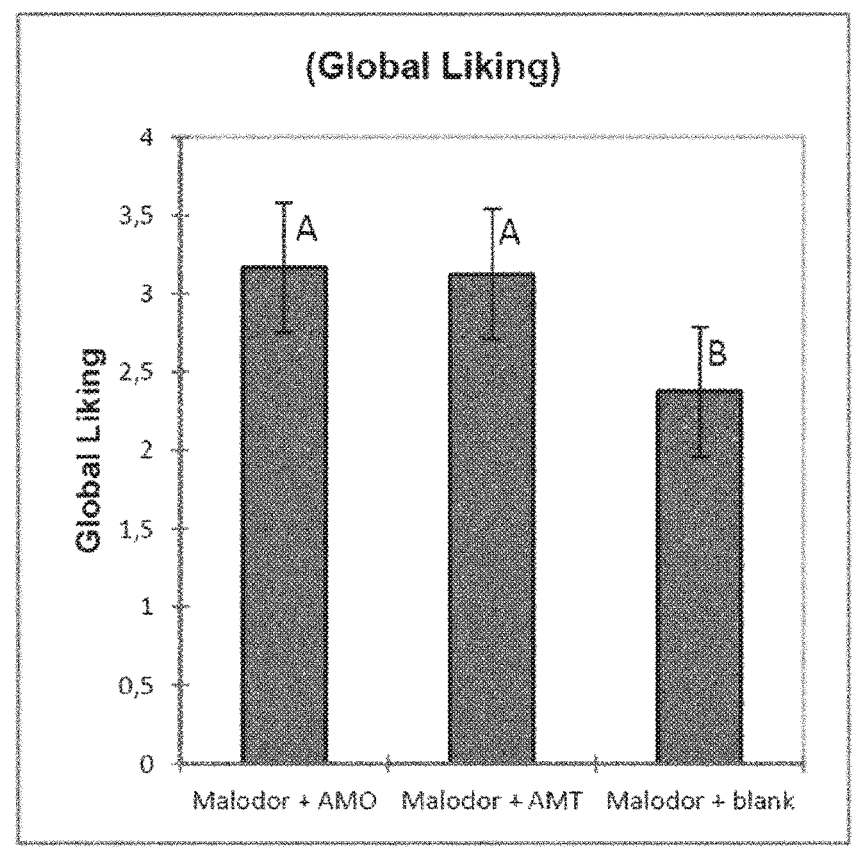

[Fig. 4C]
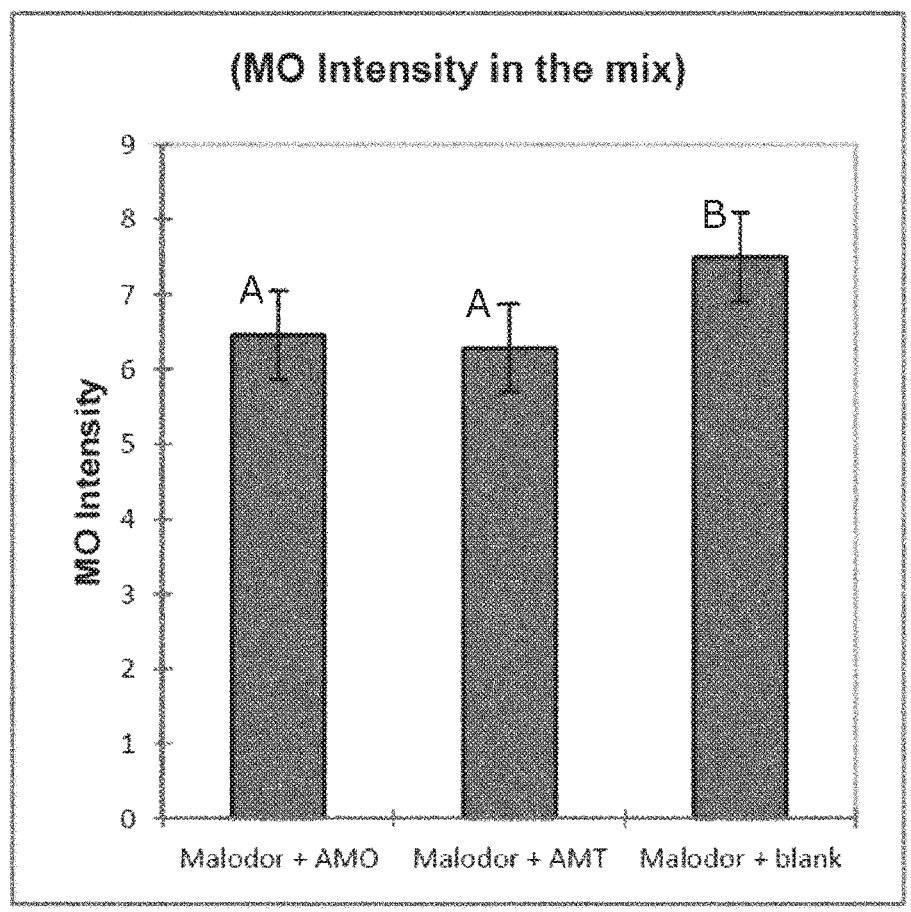

METHOD FOR IDENTIFYING MALODOUR COUNTERACTANTS

TECHNICAL FIELD

The invention relates to a method for identifying compounds that can counteract malodours, notably malodours from sulfur odorants.

BACKGROUND ART

Humans perceive an immense variety of chemicals as having distinct odours. Odour perception initiates in the nose, where odorants are detected by a large family of olfactory receptors (ORs).

The olfactory receptor proteins are members of a large family of G-protein-coupled receptors (GPCRs) arising from single coding-exon genes. Olfactory receptors share a 7-transmembrane domain structure with many neurotransmitter and hormone receptors and are responsible for the recognition and G protein-mediated transduction of odorant signals.

Volatile compounds of natural or artificial origin can be detected by a specific set of G-protein coupled receptors located in the respiratory epithelium. It has been proposed that one odorant is capable of activating multiple olfactory receptors (ORs) and that one OR is capable of detecting different odorants (NPL 1). The human genome contains ~400 intact olfactory receptor genes belonging to two main classes. Class I, "fish-like receptors" ORs presumably detect water soluble odorants, whereas class II "tetrapod specific receptors" ORs are supposed to respond to airborne volatiles (NPL 2).

A mouse olfactory receptor was recently identified, which responds to (methylthio)methanethiol in heterologous cells (NPL 3).

Human body odour is generated from natural materials present on the skin surface and secretions from the sweat and sebaceous glands. These materials are converted to characteristic odourous compound through oxidative degradation or metabolism by skin microbes.

Human apocrine sweat gland secretions are known to produce a highly individual scent upon the action of skin flora that are present in high concentrations in the armpit.

Volatile steroids, aliphatic, branched and linear fatty acids have been reported as major contributors to human axillary malodour. 3-hydroxy-3-methyl-2-hexanoic acid was in particular found to originate from a glutamine conjugate present in axillary secretions (NPL 4).

Sulfur-containing compounds have also been found to be contributors of human axillary malodour (NPL 4; NPL 5). Sulfur-containing compounds have also been identified on worn laundry from the catabolism of L-methionine (NPL 6), and from urine (NPL 7).

Sulfur containing materials are also sometimes deliberately added to consumer or industrial products as active ingredients, for example thioglycolic acid or salts and cysteine for hair treatment products, and give the product an undesirable base odour that needs to be overcome.

CITATION LIST

Non Patent Literature

[NPL 1]
Malnic B, Hirono J, Sato T, Buck L B. "Combinatorial receptor codes for odors." Cell 1999 96(5):713-23

[NPL 2]
Glusman G, Bahar A, Sharon D, Pilpel Y, White J, Lancet D. "The olfactory receptor gene superfamily: data mining, classification, and nomenclature. Mamm." Genome 2000 11(11):1016-23

[NPL 3]
Duan X, Block E, Li Z, Connelly T, Zhang J, Huang Z, Su X, Pan Y, Wu L, Chi Q, Thomas S, Zhang S, Ma M, Matsunami H, Chen G Q, Zhuang H. "Crucial role of copper in detection of metal-coordinating odorants." Proc. Natl. Acad. Sci. USA 2012 109(9):3492-7

[NPL 4]
Troccaz. "The biosynthetic pathway of sulfur-containing molecules in Human Axillary Malodor: from precursors to odorous volatiles." These de doctorat: Univ. Geneve, 2009, no. Sc. 4102 (https://archive-ouverte.unige.ch/unige:4563)

[NPL 5]
Natsch A, Schmid J, Flachsmann F. "Identification of odiferous sulfanylalkanols in human axilla secretions and their formation through cleavage of cysteine precursors by a C-S lyase isolated from axilla bacteria." Chemistry & Biodiversity 2004 1(7):1058-1072

[NPL 6]
Denawaka C, Fowlis, I, Dean J. "Source, impact and removal of malodour from soiled clothing." Journal of Chromatography A 2016 (1438): 216-225

[NPL 7]
Troccaz M, Niclass Y, Anziani P, Starkenmann C. "The influence of thermal reaction and microbial transformation on the odour of human urine." Flavour & Fragrance Journal 2013 (28): 200-211.

[NPL 8]
Li S, Ahmed L, Zhang R, Pan Y, Matsunami H, Burger J L, Block E, Batista V S, Zhuang H. "Smelling sulfur: copper and silver regulate the response of human odorant receptor OR2T11 to low-molecular-weight thiols." Journal of the American Chemical Society 2016 (doi:10.1021/jacs6b06983)

[NPL 9]
Noe F, Polster J, Geithe C, Kotthoff M, Schieberle P, Krautwurst D. OR2M3: "A highly specific and narrowly tuned human odorant receptor for the sensitive detection of onion key food odorant 3-mercapto-2-methylpentan-1-ol." Chemical Sciences 2016, 00:1-16 (doi:10.1093/chemse/bjw118)

[NPL 10]
Saito H, Kubota M, Roberts R W, Chi Q, Matsunami H. "RTP family members induce functional expression of mammalian odorant receptors." Cell 2004 119(5):679-91

[NPL 11]
Von Dannecker L E, Mercadante A F, Malnic B. "Ric-8B, an olfactory putative GTP exchange factor, amplifies signal transduction through the olfactory-specific G-protein Galphaolf." J Neurosci. 2005 Apr. 13; 25(15):3793-800

[NPL 12]
Von Dannecker L E, Mercadante A F, Malnic B. "Ric-8B promotes functional expression of odorant receptors." Proc. Natl. Acad. Sci. USA 2006 103(24):9310-4

[NPL 13]
Bufe B, Hofmann T, Krautwurst D, Raguse J D, Meyerhof W. "The human TAS2R16 receptor mediates bitter taste in response to beta-glucopyranosides." Nat. Genet. 2002 32(3):397-401

SUMMARY OF INVENTION

Technical Problem

It has now been found that a human olfactory receptor, OR4E2, responds to sulfur odorants. Accordingly the use of this polypeptide is contemplated for identifying compounds which can counteract the perception of malodour from sulfur odorants.

Solution to Problem

In one aspect, the invention relates to a method for determining whether a test compound can counteract the perceived (smelt) malodour from a sulfur odorant, the method comprising the steps of:

a) contacting the OR4E2 polypeptide with a sulfur odorant, in the presence and in the absence of the test compound under conditions permitting the binding of said sulfur odorant to OR4E2 or permitting the activation of OR4E2 by said sulfur odorant; and b) comparing the binding of OR4E2 to said sulfur odorant, or the activity of OR4E2, in the presence and in the absence of the test compound, wherein an inhibition of the binding or a decrease in activity in the presence of the test compound, relative to the binding or activity in the absence of the test compound, identifies the test compound as a compound that can counteract the perceived malodour from the sulfur odorant.

In another aspect, the invention relates to an anti-malodour composition comprising a compound identified by the above-mentioned method.

In another aspect, the invention relates to household, laundry, personal care, animal care or industrial products comprising a compound identified by the above-mentioned method, or an anti-malodour composition as defined above.

In another aspect, the present invention relates to the use of the OR4E2 polypeptide for identifying a compound that can counteract the perceived malodour from a sulfur odorant.

Advantageous Effects of Invention

In the present invention, a method for identifying compounds that can counteract malodours, notably malodours from sulfur odorants can be provided.

BRIEF DESCRIPTION OF DRAWINGS

FIG. 1A shows the response of OR4E2 to increasing concentration of a representative sulfur odorant 3-mercapto-3-methylbutanol.

FIG. 1B shows the response of OR4E2 to increasing concentration of a representative sulfur odorant diallyl trisulfide.

FIG. 2A shows the response of OR4E2 to increasing concentration of a test compound.

FIG. 2B shows the response of OR4E2 to increasing concentration of a test compound.

FIG. 3A shows the assessment (intensity) of a malodour and of test compounds.

FIG. 3B shows the assessment (pleasantness) of a malodour and of test compounds.

FIG. 4A shows the assessment (global intensity) of mixtures of a malodour with either a blank or with test compounds.

FIG. 4B shows the assessment (global pleasantness) of mixtures of a malodour with either a blank or with test compounds.

FIG. 4C shows the assessment (intensity of the presence of the malodour) of mixtures of a malodour with either a blank or with test compounds.

DESCRIPTION OF EMBODIMENTS

The invention is based on the finding that the human olfactory receptor OR4E2 responds to stimulation by sulfur odorants. Accordingly, the OR4E2 receptor is a useful tool to screen for compounds that can counteract the perceived malodour from sulfur odorants.

In one aspect, the invention provides a method for determining whether a test compound can counteract the perceived malodour from a sulfur odorant, the method comprising the steps of:

a) contacting the OR4E2 polypeptide with a sulfur odorant, in the presence and in the absence of the test compound under conditions permitting the binding of said sulfur odorant to OR4E2 or permitting the activation of OR4E2 by said sulfur odorant; and b) comparing the binding of OR4E2 to said sulfur odorant, or the activity of OR4E2, in the presence and in the absence of the test compound, wherein an inhibition of the binding or a decrease in activity in the presence of the test compound, relative to the binding or activity in the absence of the test compound, identifies the test compound as a compound that can counteract the perceived malodour from the sulfur odorant.

The method of the invention thus comprises a step of contacting the OR4E2 polypeptide with a sulfur odorant, in the presence and in the absence of the test compound under conditions permitting the binding of the sulfur odorant to OR4E2 or permitting the activation of OR4E2 by said sulfur odorant. In one embodiment, different concentrations of the sulfur odorant are used to determine the minimum effective amount which is able to activate OR4E2.

In the context of the present invention a "sulfur odorant" is a sulfur-containing compound which is a contributor of human or animal body malodour, notably human sweat malodour or human axillary malodour, or a sulfur-containing compound originating from a food source, or a sulfur-containing compound that is deliberately added to home or personal care consumer product.

In one embodiment, the sulfur odorant is selected from a sulphanyl alkanol such as 2-mercapto-3-methyl-1-butanol, 3-mercapto-2-methyl-1-pentanol, 3-mercapto-2-methyl-1-propanol, 3-mercapto-3-methyl-1-butanol, 3-mercapto-1-hexanol, 3-methyl-3(2-methyldisulfanyl)-butan-1-ol, or 3-mercapto-3-methyl-1-hexanol; a sulphanyl-aldehyde or -ketone, such as 3-mercapto-2-methylpentanal, 1-mercapto-3-pentanone, 2-mercapto-3-pentanone, or 3-mercapto-3-pentanone; a sulphanyl ester such as 3-methyl-3-mercaptobutyl acetate or 3-methyl-3-mercaptobutyl formate; a thiol such as 1-methoxyheptane-3-thiol, 4-methoxy-2-methylbutane-2-thiol, or 1-propanethiol; thioglycolic acid; dithioglycolic acid; a sulphide such as methyl-2-propenyl disulphide, 2,4-dithiapentane, dimethyl sulphide, dimethyl disulphide, dimethyl trisulphide, diallyl sulphide, diallyl disulphide, or diallyl trisulphide; allyl mercaptan; allicin; alliin; and cysteine. In a preferred embodiment the sulfur odorant is a sulphanyl alkanol or a sulphide as defined above, especially a sulphide having at least one carbon-carbon double bond, such as one or two carbon-carbon double bonds.

In one embodiment, the step of contacting the OR4E2 polypeptide with a sulfur odorant is performed in the presence of $Cu^{2+}$ ions, added as copper salt, for example an inorganic salt, e.g. $CuSO_4$, that liberates $Cu^{2+}$ ions when dissolved in water.

In one embodiment, the step of contacting the OR4E2 polypeptide with a sulfur odorant is performed in or on cells expressing said polypeptide. According to the present invention said cells can be, but are not limited to, mammalian cells, in particular human embryonic kidney cells (HEK293T), Chinese hamster ovary cells (CHO), HeLa cells or membranes preparations of said cells. The cells expressing the polypeptide can also express at least one auxiliary protein important for efficient receptor trafficking to the plasma membrane; the cells can further express a stimulatory G-protein (also called G•s), preferably a G•olf G-protein.

The OR4E2 polypeptide is defined by the sequences currently referenced in the sequence databases, as of the filing date of the present application. The skilled person in the art knows that polymorphic variants can exist within the human population. These polymorphic variants generally differ by a few amino acids (e.g., 1 to 10 amino acids).

In one embodiment, the OR4E2 polypeptide has the sequence of Sequence No. 1.

In another embodiment, the OR4E2 polypeptide has a sequence having at least 85%, such as at least 90%, at least 95%, at least 96%, at least 97%, at least 98% or at least 99% identity with Sequence No. 1, with the proviso that amino acids at positions 12, 42, 118, 165, 234, 237, 241 and 270 of Sequence No. 1 are conserved. As used herein, the term "sequence identity" means the identity of sequence between two amino acid sequences over the total length of the sequences when optimally aligned, such as by using the program ClustalW (http://www.clustal.org/; Thompson J D, Higgins D G, Gibson T J. (1994); Acids Res., 22, 4673-4680). (Gap opening penalty=10; Gap extension penalty=0.1).

In one embodiment, the OR4E2 polypeptide is encoded by a nucleic acid sequence having the sequence of Sequence No. 2.

In one embodiment, the nucleic acid sequence encoding the polypeptide OR4E2 can be included in a construct within a suitable expression vector, which is able to replicate and express the construct in a host, leading to the expression of the corresponding polypeptide. Suitable constructs are not limited provided the OR4E2 nucleic acid sequence is operably linked to an appropriate expression control sequence(s) and any other requirements to direct the expression of OR4E2. For example, the nucleic acid sequence encoding the OR4E2 polypeptide can be directly tagged or indirectly associated with a reporting system leading to a readable or measureable signal once OR4E2 is activated by ligand(s), so that the signal transduction following activation of the receptor can be detected, measured and/or monitored. Any type of reporting system can be used in the context of the invention. For example, a reporting system can be used which comprises a gene whose transcription is driven by a response element whose activity is an indication of OR4E2 activation, preferably a cAMP response element which is stimulated by adenylate cyclase which is activated by the stimulatory G-protein (G•s), such as G•olf G-protein. Any method for expressing OR4E2 can be used, and preferably transfection of the expression vector containing the construct comprising the nucleic acid sequence encoding OR4E2.

In some embodiments, the sulfur odorant may further be contacted with at least one other human olfactory receptor, selected from the OR2C1 polypeptide, the OR2T11 polypeptide and the OR2M3 polypeptide, optionally in the presence of $Cu^{2+}$ ions. The modus operandi described above with respect to the step of contacting the OR4E2 polypeptide with the sulfur odorant, can also be applied to the step of contacting the sulfur odorant with the other olfactory receptor(s). Details about the OR2C1, the OR2T11 and the OR2M3 receptors can be found in the GeneCards (registered trademark) database (http://www.genecards.org/). OR2T11 and OR2C1 have been reported to be activated by thiols (NPL 8). Also OR2M3 has been reported to be activated by thiols (NPL 9). If a given sulfur odorant activates at least one of the OR2C1, the OR2T11 and the OR2M3 polypeptides (in addition to activating the OR4E2 polypeptide) then said odorant can be regarded as an especially preferred odorant for use in the method of the invention.

The method of the invention also comprises a step of comparing the binding of OR4E2 to the sulfur odorant, or the activity of OR4E2, in the presence and in the absence of the test compound, wherein an inhibition of the binding or a decrease in activity in the presence of the test compound, relative to the binding or activity in the absence of the test compound, identifies the test compound as a compound that can counteract the perceived malodour from the sulfur odorant.

In one embodiment the test compound is identified (or not) as a compound that can counteract the perceived malodour from a sulfur odorant upon comparison of the activity of OR4E2 (contacted with the sulfur odorant) in the presence and in the absence of said test compound. As indicated above, a decrease in activity in the presence of the test compound, relative to the activity in the absence of the test compound, leads to the conclusion that the test compound is able to counteract the perceived malodour from the sulfur odorant.

Any method known in the art may be used to read or measure the response of OR4E2 to the sulfur odorant in the presence or absence of the test compound.

In one embodiment, the activity of OR4E2 is detected by using a reporting system leading to a readable or measureable signal if the test compound elicits a response of OR4E2. Reporting systems which can be used in the context of the invention include, but are not limited to, an imaging system, a fluorescence system, an enzymatic system, a binding system. For example, the following reporter systems can be used: calcium imaging with fluorescent dyes, photoproteins such as GFP, aequorin, enzymatic reporter system such as luciferase, chloramphenicol acetyltransferase, β-galactosidase, alkaline phosphatase, horse radish peroxidase, GTP-gammaS binding test, measurement of changes in cAMP levels, and the like. Advantageously, a reporting system comprising a gene whose transcription is driven by a response element whose activity is an indication of OR4E2 activation can be used, preferably the gene transcription is driven by a cAMP response element which is stimulated by adenylate cyclase which is activated by the stimulatory G-protein (G•s), such as G•olf G-protein.

In one embodiment, step b) comprises or consists of:
  i) measuring the response of OR4E2 to a control;
  ii) measuring the response of OR4E2 to the sulfur odorant in the absence of the test compound;
  iii) calculating a first fold of change [FOC1=response obtained in step ii) divided by response obtained in step i)]
  iv) measuring the response of OR4E2 to the sulfur odorant in the presence of the test compound;

v) calculating a second fold of change [FOC2=response obtained in step iv) divided by response obtained in step i)]; and vi) comparing FOC1 and FOC2, where the test compound is identified as a compound that can counteract the perceived malodour from the sulfur odorant if FOC2<FOC1.

In one embodiment, the control is a buffer used to dilute the sulfur odorant and/or the test compound.

In one embodiment, the test compound is identified as a compound that can counteract the perceived malodour from the sulfur odorant if the FOC2/FOC1 ratio obtained in step vi) is less than 0.8, such as for example less than 0.7, less than 0.5, less than 0.3, less than 0.1, less than 0.05 or less than 0.01.

In one embodiment, confirmation that a test compound identified by the method of the invention does indeed counteract the perceived malodour from a sulfur odorant, can be obtained by means of a "sniffing" test. For example, a panel of participants can be asked to separately smell the malodour from a sulfur odorant and the test compound, then to smell a mixture of the malodour and the test compound, and assess each time the intensity and pleasantness of what they have smelt. Advantageously, the malodour is smelt first, then the test compound and finally the mixture of malodour and test compound.

The method of the invention makes it possible to identify compounds that can counteract the perceived malodour from sulfur odorants and hence be incorporated into various consumer products.

In another aspect, the invention therefore relates to an anti-malodour composition comprising a compound identified by the above-mentioned method.

In another aspect, the invention relates to a household product, a laundry product, a personal care product, an animal care product, or an industrial product comprising a compound identified by the above-mentioned method, or an anti-malodour composition as defined above. Suitable products can be for domestic use, institutional use, or industrial use. Examples of such products include cat litter, laundry detergents, air care products for homes and public spaces, personal care underarm products such as deodorants, hair care/treatment products, depilatory products, foot/shoe treatment products, toilet and kitchen cleaners, farm sprays, products for rubbish/garbage bins, products for rubbish/garbage dumps, or products for sewage treatment plants.

In another aspect, the present invention relates to the use of the OR4E2 polypeptide for identifying a compound that can counteract the perceived malodour from a sulfur odorant.

The invention is illustrated by the following, non-limiting examples.

EXAMPLES

<Cell lines, Medium, and Cell Culture Conditions>

The experiments were performed using HEK293T cells (available e.g. from GE Healthcare) endogenously expressing the auxiliary protein hRTP1s, essential for efficient receptor trafficking to the plasma membrane (NPL 10; NPL 11; and NPL 12). The cell line was maintained in Dulbecco's modified Eagle Medium (DMEM, Euroclone) supplemented with 10% FBS (Fetal Bovine Serum, Euroclone cat. ECS0180L), 1% Penicillin/Streptomycin (Euroclone cat. B3001D), 50 µg/mL G418, 25 µg/mL Hygromycin, and 10 µg/mL Zeocin.

Standard propagation conditions consisted of seeding $1.5 \times 10^6$-$1.8 \times 10^6$ cells in a T75 flask twice a week, recovering about $10 \times 10^6$-$15 \times 10^6$ cells at ~80% confluence.

<Cloning of Human Olfactory Receptors>

The cDNA for OR4E2 was generated by custom gene synthesis (LifeTechnologies). The receptor DNA was then subcloned in frame 3' from a transmembrane localization epitope into a pcDNA5 expression vector (NPL 13). The correct identity of the receptor was checked by automated sequencing.

<Ligands and Buffers>

All sulfur odorants were prepared as 100 mM stock solutions using DMSO as a solvent and stored at −20° C. Copper(II) sulfate was prepared as an aqueous 30 mM stock solution. On the day of the experiment the different stock solutions were directly diluted in the assay buffer (Tyrode's buffer), the composition of which is: 5 mM KCl, 130 mM NaCl, 2 mM $CaCl_2$), 5 mM $NaHCO_3$, 1 mM $MgCl_2$, 20 mM HEPES, pH 7.4.

The odorants were used in the concentrations indicated in Table 1 below.

TABLE 1

| Compound | Concentrations used (µM) |
| --- | --- |
| 3-mercapto-3-methylbutanol | 300/150/75/30/15/7.5/3 |
| 3-methyl-3-sulfanylhexan-1-ol | 300/150/75/30/15/7.5/3 |
| dimethyl trisulfide | 300/150/75/30/15/7.5/3 |
| dithioglycolic acid | 300/150/75/30/15/7.5/3 |
| diallyl trisulfide | 300/150/75/30/15/7.5/3 |
| copper (II) sulfate | 30 |

<Instrumentation and Disposables>

The experiments were performed using FLIPR Tetra (registered trademark) High-Throughput Cellular Screening System (Molecular Devices). The cells were transfected and seeded in black 384 well polystyrene assay plates, black/clear bottom (MATRIX Part #CPL-4332).

<Transient Transfection with Lipofectamine 2000>

All transient transfections were performed with Lipofectamine 2000 (Invitrogen) according to the manufacturer's protocol. 10 µL Lipofectamine 2000 were diluted in 500 µL DMEM and incubated for 5 minutes at room temperature. In the meantime, 3 µg of plasmid DNA were diluted in 500 µL DMEM and added to the Lipofectamine 2000 mixture to obtain a final volume of 1000 µL. After incubation for 30 minutes at room temperature, the DNA-Lipofectamine complex was added to 1000 µL of a cell suspension containing 1,600,000 cells/mL. Subsequently, 25 µL per well of the complete mixture were seeded in black 384 well polystyrene assay plates. 25 µL DMEM containing 20% FBS were added to each well 3 hours post-transfection.

<Luminescence Measurement Using FLIPR Tetra (Registered Trademark)>

The cDNA for the OR4E2 receptor was co-transfected with pNL(NlucP/CRE/Hygro) (Promega). The pNL(NlucP/CRE/Hygro) vector contains a cyclic adenosine monophosphate (cAMP) response element (CRE) that drives the transcription of the luciferase reporter gene NanoLuc. The NanoLuc luciferase is a small enzyme (19.1 kDa) engineered for optimal performance as a luminescent reporter. The enzyme is about 100-fold brighter than either firefly (*Photinus pyralis*) or *Renilla reniformis* luciferase using a novel substrate, furimazine, to produce high intensity, glow-type luminescence.

In this assay, the interaction of the sulfur odorant with its cognate olfactory receptor leads to the activation of the endogenously expressed human Gαs G-protein. Gαs is a stimulatory G-protein which activates adenylate cyclase, which converts adenosine triphosphate (ATP) into cAMP. Therefore, the activity of the transcribed luciferase can be used as an indication of olfactory receptor activation.

24 hours post-transfection the medium was removed from the transfected cells and 30 μL of Tyrode's buffer containing the diluted sulfur odorant were added over 4 hours at 37° C. The cells were then transferred into an automated fluorometric imaging plate reader (FLIPR Tetra (registered trademark), Molecular Devices). 20 μL of a substrate mixture containing furimazine were then added. This addition resulted in cell lysis and allowed interaction of the luciferase with its substrate furimazine resulting in a detectable emission of light.

<Data Analysis>

The data obtained from different well replicates (n=4) were analysed with Excel, ScreenWorks, and SigmaPlot 11. The responses of the receptor to the sulfur odorants were divided by the mean responses of the receptor towards Tyrode's buffer (fold of change: FOC). The mean and standard deviation of the resulting FOC values were calculated and plotted in vertical bar charts or concentration-response curves fitted by the SigmaPlot 11 software.

<Protocol for Screening Test Compounds>

Test compounds were assessed for their inhibitory effect on OR4E2 activation. The test compounds and the controls were freshly prepared in Tyrode's buffer on the day of the experiment. All test compounds were tested at 30 μM in combination with an activating concentration of a sulfur odorant.

To avoid odorant evaporation, the compound test plates were prepared just 2-3 hours before screening. Accordingly, the compounds were directly pipetted with a 384 pipetting head from the mother plates into the screening plates containing an appropriate amount of Tyrode's buffer. Then, the controls and the sulfur odorant were added to the wells. The prepared compound plates were then transferred onto the transfected cell plates and incubated for 3-4 hours at 37° C. followed by a 30 minutes equilibration period at room temperature prior to reading. This procedure generates uniform signals and avoids an umbrella like pattern, which is sometimes observed in luminescence read-outs.

The test compound screening was performed in triplicate. The obtained data from the different well replicates were analysed with a GeneData Screener. Mean FOC1 values of the triplicates of each individual compound in combination with the sulfur odorant were set into relation to the activity value obtained for the sulfur odorant in the absence of any test compound (FOC2).

Example 1

To investigate the response of OR4E2 to the five sulfur odorants of Table 1, the cells were transiently transfected with plasmid DNA for the receptor. 24 hours after transfection, the cells were stimulated with seven different concentrations of the sulfur odorants (see Table 1). 4 hours post-stimulation, the cells were lysed with the substrate mixture and luciferase activity was detected. FIGS. 1A and 1B show the response of OR4E2 to increasing concentrations of 3-mercapto-3-methylbutanol and diallyl trisulfide, respectively. Both odorants had a positive effect on OR4E2 activation.

Example 2

Cells were transiently transfected with plasmid DNA for OR4E2. 24 hours after transfection, the cells were stimulated with seven different concentrations of the following test compounds: *Tagetes minuta* 1. flower oil or flower extract (CAS No. 8016-84-0, respectively 91770-75-1), and opoponax oil (CAS No. 8021-36-1). Stimulation was done in the presence of 300 μM of the OR4E2 activator 2,4 dithiapentane. 4 hours post-stimulation, the cells were lysed with the substrate mixture and luciferase activity was detected. Moreover, the test compounds were also tested on cells that do not express OR4E2 (mock). Those cells were stimulated with the same test compounds in the presence of 30 nM isoproterenol to control for not OR4E2 related inhibitory effects of the test compounds. The obtained data from the different well replicates were analysed with Graphpad PRISM by calculating mean and standard deviation. The response of OR4E2 to 2,4 dithiapentane in the absence of any test compound was set to 100% and concentration-response curves were calculated.

FIGS. 2A-2B show the response of OR4E2 transfected cells (dot) and control cells (square) to increasing concentrations of the above-mentioned compounds (*Tagetes minuta* 1., respectively opoponax oil) in the presence of 300 μM 2,4-dithiopentane (OR4E2) or 30 nM isoproterenol (mock), respectively.

Example 31

To illustrate the active effect of some compounds against malodour, a test was designed to evaluate their efficacy.

Participants

The testing included 24 participants. They were all able to smell, and were given detailed information about the test before accepting to participate. Women were not pregnant.

Methods

The test used a series of 6×60 mL jar with one or two wicks saturated with a molecule inside. The first three jars respectively contained the malodour alone (3-mercapto-2-methyl butanol), compound T* (AMT) alone, and compound O* (AMO) alone. The three other jars contained mixtures of compounds: "Malodour+blank (nothing)", "Malodour+AMT", and "Malodour+AMO". The concentration of the malodour was set to be close to real life. The intensities of the test compounds were set to match that of the malodour.

(* T=*Tagetes minuta* 1., O=opoponax oil, as identified in example 2).

The testing was done in 3 parts. In the first part, participants begun the testing by smelling the Malodour alone and rated it for intensity on an intensity scale from 0 "I smell nothing" to 9 "extremely strong" and for liking on an intensity scale from 0 "extremely unpleasant" to 9 "extremely pleasant". They were also told to smell long enough so as to be able to recognize it further down in the test.

In the second part, the participant smelled the two test compounds in a randomized order. They were asked to rate again for intensity of what they smelled and for the liking.

In the third part, participants smelled the mixtures in randomized order and rated the global intensity of the odour inside the jar and the global liking of what they smelled.

They also had to rate the intensity of the presence of the malodour on an intensity scale from 0 "the malodour is not present" to 9 "the malodour is extremely strong".

Results

The results of the first two parts of the test are shown in FIGS. 3A-3B. FIG. 3A shows the intensity score for each compound alone in the jar. FIG. 3B shows the liking score for each compound alone in the jar. Bars linked with a same letter are not different (Duncan test at 95%). The error bar shows the confidence interval at 95%. ANOVA analysis showed that the malodour was more intense ($F=10.49$, $p<0.01$) and more unpleasant ($F=9.16$, $p<0.01$) than the two test compounds.

The results of the third part of the test are shown in FIGS. 4A-4C. FIG. 4A shows that the global intensity was not different for the three jars with a mixture of molecules inside. ANOVA analysis was not significant. However, ANOVA analysis showed that the Malodour alone (combined with blank) was judged less pleasant than the two mixtures malodour+test compound (see FIG. 4B) ($F=3.20$, $p<0.05$). FIG. 4C shows that the presence of the malodour is not evaluated in the same way when it is combined with a test compound. Its intensity is lower when combined with a test compound ($F=3.28$; $p<0.05$).

Taken together, these results show that compounds which activate the OR4E2 receptor allow a reduction of the intensity of the targeted malodour when combined with said malodour. This test demonstrates that the effect is not due to a difference of intensity. When judged alone, the test compounds are perceived as less intense than the malodour. When judged in a mixture, the different mixtures are not different in intensity. The liking assessment shows that the test compounds are not overly pleasant. The global liking shows that the combination of each of the test compounds with the malodour decreases the unpleasantness. It also diminishes the intensity of the malodour detected in the mixtures.

While the invention has been described in detail and with reference to specific embodiments thereof, it will be apparent to one skilled in the art that various changes and modifications can be made therein without departing from the spirit and scope thereof. This application is based on European Patent Application No. 16306680.6 filed on Dec. 14, 2016, the entire subject matter of which is incorporated herein by reference.

INDUSTRIAL APPLICABILITY

In the present invention, it is possible to provide a method for identifying compounds that can counteract malodours, notably malodours from sulfur odorants.

The invention claimed is:

1. A method for determining whether a test compound can counteract a perceived malodour from a sulfur odorant, the method comprising the steps of:
   a) contacting cells expressing an OR4E2 polypeptide with the sulfur odorant in the presence and in the absence of the test compound;
   b) measuring an activity of the OR4E2 polypeptide in the presence and in the absence of the test compound under an identical condition;
   c) comparing the activity of the OR4E2 polypeptide in the presence of the test compound to the activity of the OR4E2 polypeptide in the absence of the test compound;
   wherein a decrease in the activity of the OR4E2 polypeptide in the presence of the test compound relative to the activity of the OR4E2 polypeptide in the absence of the test compound identifies the test compound as a compound that can counteract the perceived malodour from the sulfur odorant;
   wherein the sulfur odorant is selected from the group consisting of: a sulfanyl alkanol selected from the group consisting of 2-mercapto-3-methyl-1-butanol, 3-mercapto-2-methyl-1-pentanol, 3-mercapto-2-methyl-1-propanol, 3-mercapto-3-methyl-1-butanol, 3-mercapto-1-hexanol, 3-methyl-3(2-methyldisulfanyl)-butan-1-ol and 3-mercapto-3-methyl-1-hexanol; and a sulfide selected from the group consisting of methyl-2-propenyl disulfide, 2,4-dithiapentane, dimethyl sulfide, dimethyl disulfide, dimethyl trisulfide, diallyl sulfide, diallyl disulfide and diallyl trisulfide; and wherein the activity of the OR4E2 polypeptide is measured using a reporting system capable of producing a readable or measurable signal.

2. The method of claim 1, wherein said cells are mammalian cells.

3. The method of claim 2, wherein said mammalian cells are selected from human embryonic kidney cells, Chinese hamster ovary cells and HeLa cells.

4. The method of claim 1, wherein step a) is performed in the presence of $Cu^{2+}$ ions.

5. The method of claim 1, wherein the OR4E2 polypeptide has the sequence of SEQ ID NO: 1.

6. The method of claim 1, wherein the OR4E2 polypeptide is encoded by a nucleic acid having the sequence of SEQ ID NO: 2.

7. The method of claim 1, wherein the reporting system comprises a gene whose transcription is driven by a cAMP response element which is stimulated by adenylate cyclase which is activated by a stimulatory G-protein.

8. A method for determining whether a test compound can counteract a perceived malodour from a sulfur odorant, the method comprising the steps of:
   a) providing cells expressing an OR4E2 polypeptide;
   b) measuring a magnitude of a response of the OR4E2 polypeptide to control conditions;
   c) contacting said cells with the sulfur odorant in the presence and in the absence of the test compound under an identical condition;
   d) measuring a magnitude of a response of the OR4E2 polypeptide to the sulfur odorant in the absence of the test compound under an identical condition;
   e) calculating a first fold of change (FOC1), wherein FOC1 equals the magnitude of the response measured in step d) divided by the magnitude of the response measured in step b);
   f) measuring a magnitude of a response of the OR4E2 polypeptide to the sulfur odorant in the presence of the test compound under an identical condition;
   g) calculating a second fold of change (FOC2), wherein FOC2 equals the magnitude of the response measured in step f) divided by the magnitude of the response measured in step b);
   h) comparing FOC1 with FOC2; and
   i) identifying the test compound as a compound that can counteract the perceived malodour from the sulfur odorant if a ratio FOC2/FOC1 is less than 0.8;
   wherein the sulfur odorant is selected from the group consisting of: a sulfanyl alkanol selected from the group consisting of 2-mercapto-3-methyl-1-butanol, 3-mercapto-2-methyl-1-pentanol, 3-mercapto-2-methyl-1-propanol, 3-mercapto-3-methyl-1-butanol, 3-mercapto-1-hexanol, 3-methyl-3(2-methyldisulfanyl)-butan-1-ol and 3-mercapto-3-methyl-1-hexanol; and a sulfide selected from the group consisting of methyl-2-propenyl disulfide, 2,4-dithiapentane, dimethyl sulfide, dimethyl disulfide, dimethyl trisulfide, diallyl sulfide, diallyl disulfide and diallyl trisulfide.

9. The method of claim 8, wherein the test compound is identified as the compound that can counteract the perceived malodour from the sulfur odorant if the ratio FOC2/FOC1 is less than 0.7.

* * * * *

SEQUENCE LISTING

<160> NUMBER OF SEQ ID NOS: 2

<210> SEQ ID NO 1
<211> LENGTH: 313
<212> TYPE: PRT
<213> ORGANISM: Homo sapiens
<220> FEATURE:

<400> SEQUENCE: 1

```
Met Asp Ser Leu Asn Gln Thr Arg Val Thr Glu Phe Val Phe Leu Gly
1               5                   10                  15

Leu Thr Asp Asn Arg Val Leu Glu Met Leu Phe Phe Met Ala Phe Ser
                20                  25                  30

Ala Ile Tyr Met Leu Thr Leu Ser Gly Asn Ile Leu Ile Ile Ile Ala
            35                  40                  45

Thr Val Phe Thr Pro Ser Leu His Thr Pro Met Tyr Phe Phe Leu Ser
        50                  55                  60

Asn Leu Ser Phe Ile Asp Ile Cys His Ser Ser Val Thr Val Pro Lys
65                  70                  75                  80

Met Leu Glu Gly Leu Leu Leu Glu Arg Lys Thr Ile Ser Phe Asp Asn
                85                  90                  95

Cys Ile Thr Gln Leu Phe Phe Leu His Leu Phe Ala Cys Ala Glu Ile
            100                 105                 110

Phe Leu Leu Ile Ile Met Ala Tyr Asp Arg Tyr Val Ala Ile Cys Thr
        115                 120                 125

Pro Leu His Tyr Pro Asn Val Met Asn Met Arg Val Cys Ile Gln Leu
    130                 135                 140

Val Phe Ala Leu Trp Leu Gly Gly Thr Val His Ser Leu Gly Gln Thr
145                 150                 155                 160

Phe Leu Thr Ile Arg Leu Pro Tyr Cys Gly Pro Asn Ile Ile Asp Ser
                165                 170                 175

Tyr Phe Cys Asp Val Pro Leu Val Ile Lys Leu Ala Cys Thr Asp Thr
            180                 185                 190

Tyr Leu Thr Gly Ile Leu Ile Val Thr Asn Ser Gly Thr Ile Ser Leu
        195                 200                 205

Ser Cys Phe Leu Ala Val Val Thr Ser Tyr Met Val Ile Leu Val Ser
    210                 215                 220
```

```
Leu Arg Lys His Ser Ala Glu Gly Arg Arg Lys Ala Leu Ser Thr Cys
225                 230                 235                 240

Ser Ala His Phe Met Val Val Ala Leu Phe Phe Gly Pro Cys Ile Phe
                245                 250                 255

Ile Tyr Thr Arg Pro Asp Thr Ser Phe Ser Ile Asp Lys Val Val Ser
            260                 265                 270

Val Phe Tyr Thr Val Val Thr Pro Leu Leu Asn Pro Phe Ile Tyr Thr
        275                 280                 285

Leu Arg Asn Glu Glu Val Lys Ser Ala Met Lys Gln Leu Arg Gln Arg
    290                 295                 300

Gln Val Phe Phe Thr Lys Ser Tyr Thr
305                 310

<210> SEQ ID NO 2
<211> LENGTH: 939
<212> TYPE: DNA
<213> ORGANISM: Homo sapiens
<220> FEATURE:

<400> SEQUENCE: 2
atggacagtc taaaccaaac aagagtgact gaatttgtct tcttgggact cactgataac      60
cgggtgctgg aaatgctgtt tttcatggca ttctcagcca tttatatgct aacgctttca     120
gggaacattc tcatcatcat tgccacagtc tttactccaa gtctccatac ccccatgtat     180
ttcttcctga gcaatctgtc ctttattgac atctgccact catctgtcac tgtgcctaag     240
atgttggagg gtttgctttt agaaagaaag accatttcct ttgacaactg catcacacag     300
ctcttcttcc tacatctctt tgcctgtgcc gagatctttc tgctgatcat tgtggcgtat     360
gatcgttacg tggctatctg cactccactc cactacccca atgtgatgaa catgagagtc     420
tgtatacagc ttgtctttgc tctctggttg gggggtactg ttcactcact agggcagacc     480
ttcttgacta ttcgtctacc ttactgtggc cccaacatta ttgacagcta cttctgtgat     540
gtgcctcttg ttatcaagct ggcctgcaca gatacatacc tcacaggaat actgattgtg     600
accaatagtg gaaccatctc cctctcctgt ttcttggccg tggtcacctc ctatatggtc     660
atcctggttt ctcttcgaaa acactcagct gaagggcgcc agaaagccct gtctacctgc     720
tcggcccact tcatggtggt tgccctcttc tttgggccat gtatcttcat ctatactcgg     780
ccagacacca gcttctccat tgacaaggtg gtgtctgtct tctacacagt ggtcacccct     840
ttgctgaatc ccttcattta caccttgagg aatgaggagg taaaaagtgc catgaagcag     900
ctcaggcaga gacaagtttt tttcacgaaa tcatataca                            939
```